United States Patent [19]

Claude

[11] Patent Number: 5,084,022
[45] Date of Patent: Jan. 28, 1992

[54] GRADUATED GUIDEWIRE
[75] Inventor: Timothy J. Claude, Coon Rapids, Minn.
[73] Assignee: Lake Region Manufacturing Company, Inc., Chaska, Minn.
[21] Appl. No.: 417,783
[22] Filed: Oct. 4, 1989
[51] Int. Cl.$^5$ ............................................. A61M 5/178
[52] U.S. Cl. .................................... 604/164; 604/117; 128/772
[58] Field of Search .................... 128/772, 657, 658; 604/164, 280, 167; 264/230, DIG. 71

[56] References Cited
U.S. PATENT DOCUMENTS

| | | | |
|---|---|---|---|
| 4,500,313 | 2/1985 | Young | 604/280 |
| 4,671,291 | 6/1987 | Wilson | 604/280 |
| 4,773,432 | 9/1988 | Rydell | 128/772 |
| 4,863,423 | 9/1989 | Wallace | 604/280 |
| 4,917,104 | 4/1990 | Rebell | 128/772 |
| 4,951,686 | 8/1990 | Herlitze | 604/280 |

Primary Examiner—Stephen C. Pellegrino
Assistant Examiner—Michael Rafa
Attorney, Agent, or Firm—Clayton R. Johnson

[57] ABSTRACT

Disclosed herein are various types of guidewires that are provided with spaced indicia to indicate the distance that a guidewire is extended into a vascular vessel, catheter or other instruments. That is, there are disclosed J-type, linear type and steerable type guidewires. Preferably the indicia is made up of a system of marks to indicate various units of measurements, for example units of 10, with narrow bands representing the units such as 10, 20, 30 and 40 while wider bands represent units of 50. If the guidewire is a double ended guidewire then the indicia would represent progressively higher indicia from each end of the linear part of the guidewire. Preferably the marks are formed by electrochemical etching of the metal wire forming at least a part of the guidewire and if desired may be provided with a clear plastic coating that is non-toxic and biocompatible. The marks may be formed by other process, for example laser treatment.

7 Claims, 3 Drawing Sheets

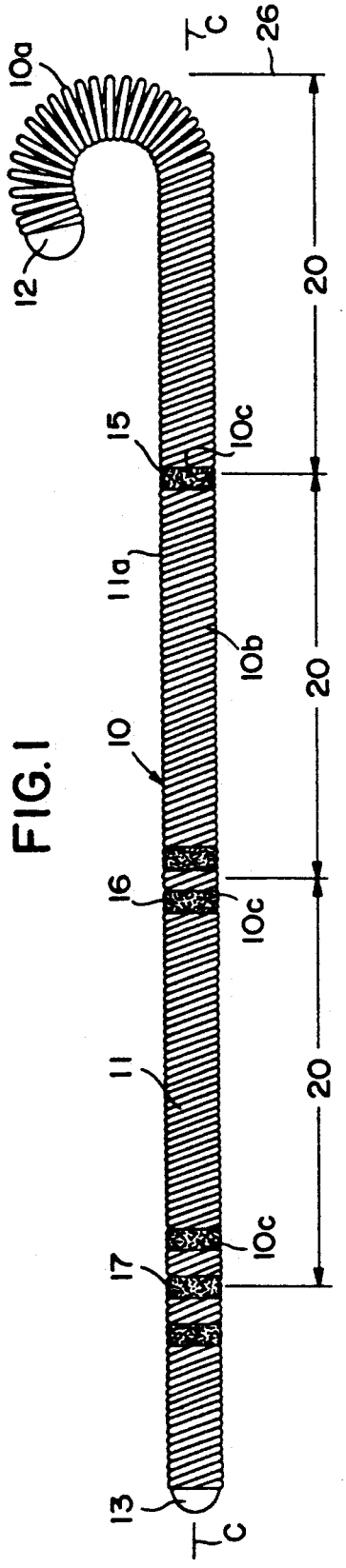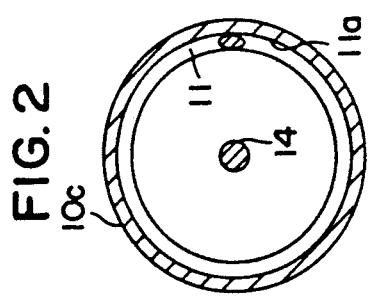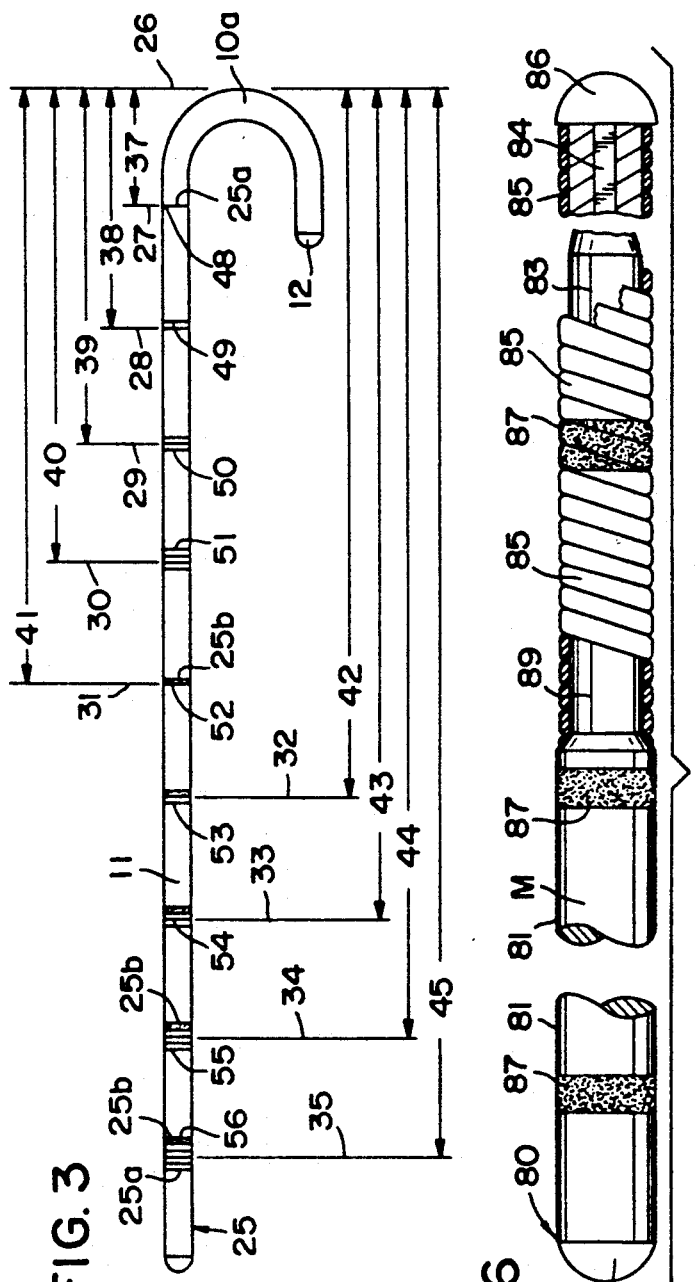

GRADUATED GUIDEWIRE

BACKGROUND OF THE INVENTION

This invention relates to facilitating a determination of the distance a guidewire extends into, for example a vascular vessel or a catheter.

It is old to use electro-chemical equipment, for example, such as sold by Marking Methods, Inc. for providing indicia on medical equipment, including permanent implants such as pacemaker cases with serial numbers for traciablity. In U.S. Pat. No. 3,399,668 to Lundgren there is disclosed a cholangiography catheter having substantially equally spaced indicia such that the surgeon may determine the extent of insertion of the catheter in a cystic duct while U.S. Pat. No. 4,645,491 to Evans discloses providing circular bands on a catheter with each band being distinguished from other bands by color. U.S. Pat. No. 4,397,091 to Gustavsson in column 1 discloses problems incurred in providing readable graduations on a catheter. U.S. Pat. No. 4,500,313 to Young discloses a urethral catheter having an outer sleeve member and an inner tubular member that is insertable into the sleeve member and has a section with calibrated markings, while U.S. Pat. No. 4,559,046 also discloses providing indicia on a catheter.

Physicians and other medical personal have had need to know the distance that a guidewire extends into a vascular vessel, catheter or other medical instrumentation. In order to help facilitating overcoming this problem, this invention has been made.

SUMMARY OF THE INVENTION

The invention disclosed herein is directed to providing guidewires with indicia or markings at predetermined locations along at least a substantial portion of the axial length thereof that are readily readable by medical personal in order to ascertain the distance that the guidewire extends into a body (lumen) vessel, or catheter or other medical instrumentation. Preferably the indicia is provided by electro-chemically etching a metal guidewire.

BRIEF DESCRIPTION OF THE DRAWINGS

FIG. 1 is a side view of a convential J-type guidewire that is provided with the graduated indicia of this invention;

FIG. 2 is a cross sectional view of the guidewire of FIG. 1 axially intermediate the opposite end portions guidewire beads) thereof with the radial thickness of the etched band relative to the remainder of the coil wires being exaggerated.

FIG. 3 is a schematic showing of a guidewire of FIG. 1 with a second embodiment of indicia thereon indicating the distance from the distal-most part of the curved part of the J-shaped portion toward the proximal end;

FIG. 6 is a side view of the fifth embodiment of the guidewire of the invention which is a steerable type guidewire.

Referring to FIGS. 1 and 2, the first embodiment of the invention, generally designated 10, includes a guidewire having a helically wound, metal guidewire coil 11. The coil has a generally J-shaped distal end portion 10a which at its distal terminal end mounts a distal guidewire tip or bead 12. The axially elongated, generally linear portion 10b of the coil at its proximal terminal end mounts a proximal guidewire tip or bead 13. The linear portion of the coil has a linear central axis C—C. Advantageously the guidewire includes a core wire and/or safety wire 14 that is joined to the proximal tip and to the distal tip and/or the distal end portion of the coil.

Figure 4:
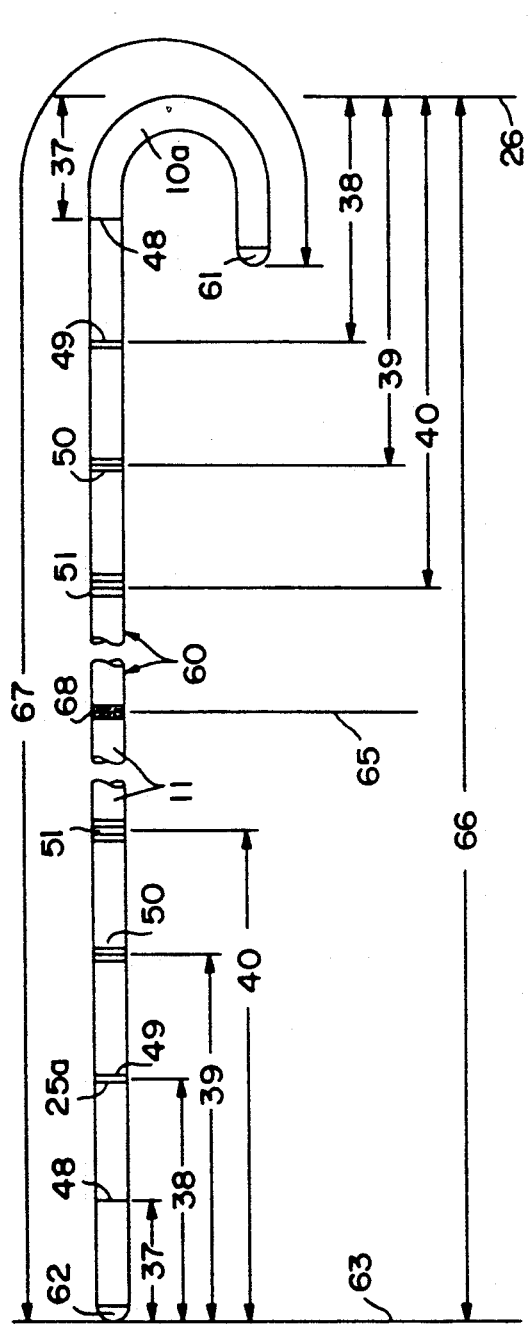
FIG. 4 is a schematic showing of the guidewire of FIG. 1 other than it has a third embodiment of indicia provided thereon and is for the type of guidewire used as a double ended guidewire.

The guidewire as shown in FIG. 1 has three indicia 15, 16, 17 provided thereon, the indicia 15, 16, 17 respectively being made up of one, two and three marks 10c respectively. Advantageously, although not essential, the axial center of each indicia is equally spaced from the axial center of the axially adjacent indicia, for example an axial dimension 20 that may be 10 cm. That is the spacing as shown is from the Center of one set of marks to the center of the axially adjacent set of marks. The rightward-most indicia in FIG. 1 is also axially spaced from the extension line 26 that extends tangentially to the distal-most part of the J-portion in its relaxed position that is shown in FIG. 1. Desirably the marks extend entirely around the outer circumference of the coil and are in the form of bands, however, other shape marks may be used, or bands, if used, can extend only partially around the coil. Preferably the markings are formed by electro-chemically etching the marks on the wire coil. For example the guidewire may be etched by placing the portion of the coil to be etched on a stencil with a pad containing the chemical to be used being between the stencil and a block (for example made of carbon). The stencil has slots therein that are spaced in accordance with the marks to be formed. With the coil being between the stencil and plate, the chemical is applied by rolling the coil over the stencil with a plate so that the chemical is force through slots and against the coil if circumferential bands are to be formed, the plate and block being connected across a source of electricity. The chemical is applied through the stencil slots to result in a combination of metal oxide and electrolyte salts that define marks on the outer circumferential surface portion 11a of the guidewire member to represent the desired indicia. The chemical compound used would depend upon the metal to be etched. For example if the metal is stainless steel the chemical could be a potassium compound. After the guidewire is etched the guidewire is cleaned to remove any toxic or other undesirable compounds from the guidewire.

The electro-chemical method can only be used on guidewires that are not coated by Teflon (polytetrofluoroethylene material) or similar type coatings. However, the guidewires can be electro-chemically etched and then coated with clear Teflon, hydrophyllic polymer or other clear or transparent coating material such as heparin.

Other methods may be used for forming the marks, for example an ink, epoxy, lasers, spraying, Teflon and colored hydrophylic polymer as long as there is met the criteria that follows:
  a. Is non-toxic and bio-compatibe.
  b. Will not scrape or rub off due to normal use.
  c. Are visible at arms length, preferably at least 12" from the unaided eye at normal room lighting.
  d. Must be good for the shelf life of the guidewire.
  e. Must be consistently reproducible in a production setting.

Teflon coated guidewires can be successfully provided with marks by laser etching, for example by masking such that only the areas that are to be etched are exposed to the laser treatment. Usually the laser etching would not extend radially all the way through the coating. The entire etched coated guidewire can be, if desired, coated with a suitable layer of transparent material to provide a graduated guidewire.

To date the electo-chemical and laser etching processes are preferred with the electo-chemical process being preferred over the laser process in that the laser etching process presently is slower and more expensive in production type operations.

Referring to FIG. 3 wherein the guidewire, generally designated 25, is the same as shown in FIG. 1 other than for the widths of the various bands thereon, the extension line 26 that extends perpendicular to the central axis of the linear portion of the guidewire being tangential to the distal-most part of the J-portion in its relaxed condition. With the guidewire being a single ended type, and for example if the axial center of adjacent indicia are spaced by 10 cms., and the length of the linear part of the guidewire, together with of the curved part of portion 10a joined thereto, to the extension line 26 being at least 100 cms., than, for example the extension lines 27-35 vertically adjacent to the axial centers of indicia 48 through 56 respectively are respectively spaced from line 26 by dimensions 37-45. That is each of the narrow bands 25a represents a unit of 10 cms. while each of the wide bands represents a unit of 50 cms. Each of the narrow bands may be of a 2 mm width while each of the wide bands may be of a 4 mm. width. In accordance with this example the leftward-most indicia 56 in FIG. 3 represents 90 cms. from extension line 26 while the rightward-most indicia 48 represents 10 cms.

Referring to FIG. 4 wherein the guidewire, generally designated 60, advantageously may be the same as that shown in FIG. 3 other than it is to be used as a double end guidewire. Accordingly the guidewire 60 has the indicia thereon in a different pattern than that provided on the guidewire of FIG. 3. With the guidewire in its relaxed condition and assuming the axial length of the guidewire is 67 and the linear length from the proximal terminal part of the bead 62 (extension line 63) to the extension line 26 is 66, there is provided an axial center indicia 68, i.e. midway between the extension lines 26, 63. If the axial dimension of the other indicia on the guidewire are of the same axial dimensions referred with reference to FIG. 4 then advantageously the center indicia 68 may be of an axial dimension of 9 mm. If the guidewire 60 is to have the bead 62, which is joined to the terminal end of the linear portion of the guidewire, extended into a vascular vessel, than the indicia 48 to 51 at the left end portion of the guidewire as shown in FIG. 4 represent progressively higher units in a rightward direction; while if the bead 61 at the terminal end portion of the coil that forms the J-portion is to be inserted into the vessel, than the indicia 48 to 51 on the right end portion as shown in FIG. 4 represents progressively higher units in a leftward direction. The extension line (center line) 65 represents the axial center of the indicia 68.

Figure 5:
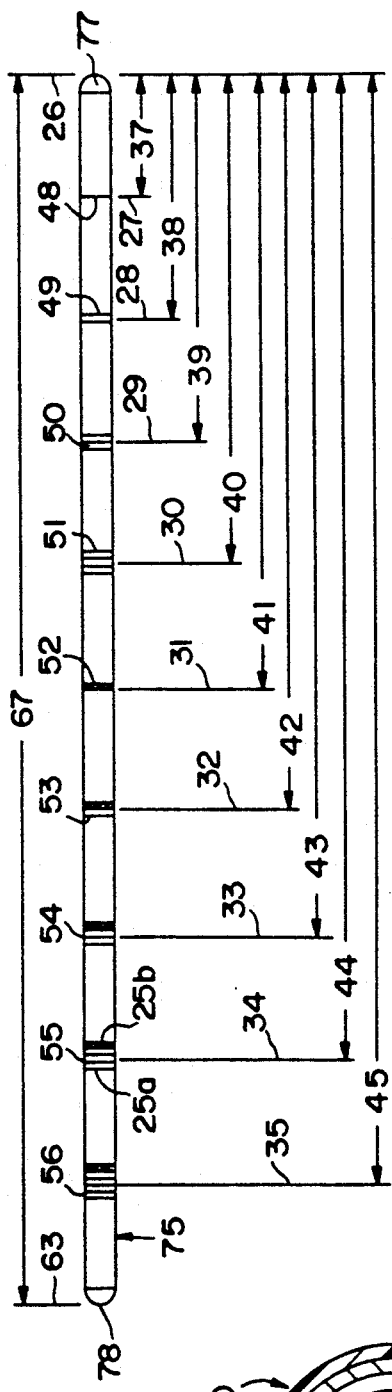
FIG. 5 is both a plan and a side schematic showing of a fourth embodiment of the guidewire of the invention which is a linear type guidewire.

Referring to FIG. 5, there is shown a linear type guidewire, generally designated 75, that includes a coil spring 76 (individual coils not being shown), a distal terminal tip (bead) 77 mounted by the distal end portion of the coil and a proximal terminal tip (bead) 78 mounted by the proximal terminal end portion of the coil spring. Advantageously indicia 48 through 56 may be provided on the guidewire with the extension line 26 extending tangentially to the distal-most part of the distal tip. Further the spacing of the indicia from the extension line 26 may be of dimensions 37 through 45.

The indicia of this invention also may be provided on a steerable type guidewire, one example of such a type of guidewire being fragmentarily shown in FIG. 6 and generally designated 80. The guidewire 80 includes a core or main wire M having an enlarged diameter proximal cylindrical end potion with a proximal tip 82 joined to the proximal end thereof. The portion 81 is joined to an axially intermediate portion 89 that is of a smaller diameter than portion 81 while portion 89 may be joined to a portion 83 that is of the same or smaller diameter than that of portion 89. Portion 83 is joined through the main wire distal end portion and/or safety wire 84 to the distal tip 86. A helically wound coil spring 85 that has an outer diameter substantially the same as that of portion 81 is joined to portion 81 while the axial opposite end of the spring is joined to one or both of portion 84 and the distal tip 86. The axial length of the portion 81 may be many times greater than that of the remainder of the guidewire. The guidewire 80 may be of a number of conventional type steerable type guidewires other than for the provision of indicia provide thereon in accordance with this invention. The guidewire has indicia 87 provided on the outer circumferential surface of both of the portion 81 and the coil spring 85. The axial spacing of the axially adjacent indicia from the distal-most part of the distal tip may be the same such as described with reference to FIG. 4 other than the indicia represents progressively higher units from the distal tip toward the proximal tip. The actual markings making up each indicia would depend upon the length of the guidewire and the axial spacing of the indicia.

Figure 7:
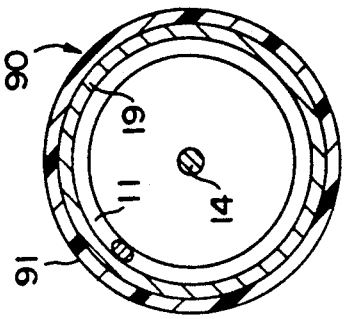
FIG. 7 is a cross sectional view of a sixth embodiment of the invention with the radial thickness of the etched band relative to the remainder of the coil wire being exaggerated as is the radial thickness of the coating.

Referring to FIG. 7, the embodiment thereof may be the same as previously described embodiments with reference to other embodiments than after the coil 11 has been provided with etching 19, a clear plastic coating 91 is provided on the guidewire to extend at least a part of the axial length thereof. The coatings may be of the types such as previously referred to.

If the coding of the indicia follows the same system shown in FIGS. 2, 3 and 5, than to represent 100 cm., two wide marks 25b could be used while 110 cm. could be two wide marks plus a narrow mark 25a. Even though the axially adjacent indicia has been described a being equally spaced, it is to be understood that the spacing could be varied as long as it represented the desired units. Further the units represented could be units other than units of 10, and the marks instead of circular bands could be, for example dots, or other shaped marks may be used whereby the same pattern and scales are provided such as previously described.

In using the invention if the graduated guidewire is extended through a catheter that is extended into a vascular vessel, by knowing the distance that the exposed part of the catheter extends outwardly of the vessel and subtracting the dimension of the exposed part from the exposed indicia on the guidewire, one can readily ascertain the distance the guidewire extends into the vessel.

After a catheter has been inserted into a vessel, at times it is desired to know when the distal terminal end of the guidewire is at the distal terminal end of the catheter. Accordingly a mark can be provide on the guidewire that is radially aligned with the proximal terminal end of the catheter when the distal terminal end of the catheter and the distal terminal end of the guidewire are radially aligned. Further if it is desired to know when the guidewire distal terminal end has been extended a predetermined distance distally beyond the catheter distal terminal end, than advantageously a second mark is provided on the guidewire that is axially spaced in a proximal direction from the first mark mentioned in this paragraph by said predetermined distance. Advantageously the marks referred to in this paragraph as well as additional marks, if desired, may be provided on a guidewire by a masking process such as described with reference to the seventh or eighth embodiments, or by one of the other embodiments that have been previously described.

Figure 8:
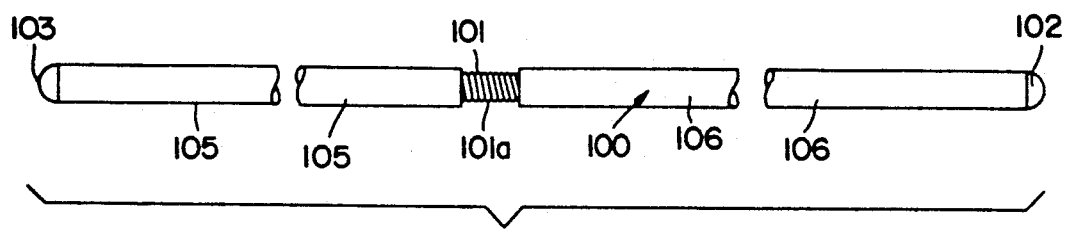
FIG. 8 is a side view of a seventh embodiment of the invention with axial intermediate parts broken away.
Figure 9:
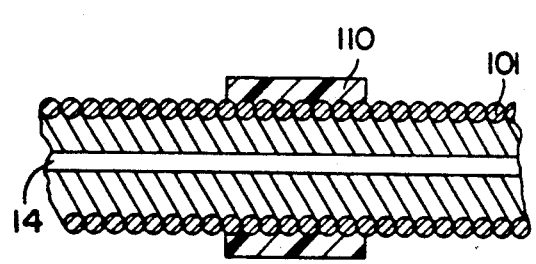
FIG. 9 is fragmentary cross section view showing a step in making the guidewire of FIG. 8, the thickness of the band relative to diameter of coil wires being exaggerated.
Figure 10:
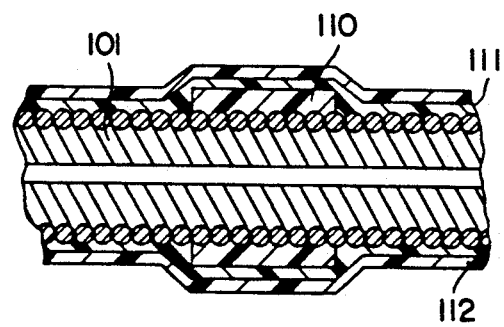
FIG. 10 is a fragmentary cross sectional view showing a subsequent step in making the guidewire FIG. 8.

Referring to FIGS. 8–10, the seventh embodiment, generally designated 100, includes an axially elongate spring coil 101 having a distal tip 102, a proximal tip 103, an uncoated axially intermediate portion 101a, an annular coating (sheath) 105 extending axially from the proximal tip to axially intermediate coil portion 101a and an annular coating 106 extending axially from the distal tip to the portion 101a. In making the guidewire 100, an uncoated spring coil 101 having distal and proximal tips joined thereto have a heat shrinkable plastic band 110, desirable made of Teflon, placed on the spring coil to mask the portion (portion 101a) at the position that the marking is desired. The heat shrinkable film is heated to shrink sufficiently to remain at the desired location on the spring coil. After the band is sufficiently shrunk, the coil, including the band, is sprayed with a annular coating of curable, non-heat shrinkable Teflon primer 111 extending axially from one tip to the other. Thereafter the primed coil, including the band, is sprayed with a curable, non-heat shrinkable Teflon enamel for forming an annular coating 112 extending axially from one tip to the other, both of the primer and enamel advantageously being a water based type. Thence the coated guidewire is place in an oven to heat the coated guidewire to cure the curable Teflon. While the curable Teflon is being cured the band 110 together with the portion of the coating thereon tears and/or breaks to separate from the guidewire coil whereby the uncoated portion 101a is axially between the coatings 105 and 106. The uncoated portion serves as a mark in the desired location on the guidewire, for example to indicate that the guidewire has been inserted into a catheter to have the catheter and guidewire distal terminal ends radially aligned.

Figure 11:
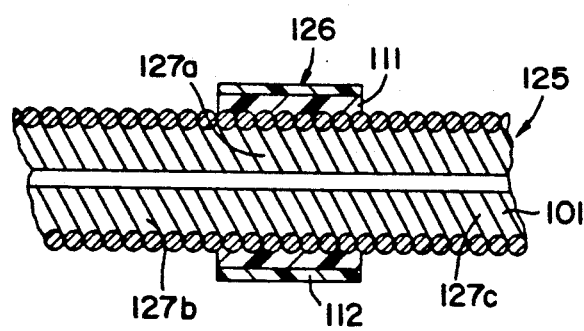
FIG. 11 is a cross sectional view of the eighth embodiment of the invention with axial intermediate parts broken away, the thickness of the non-heat shrinkable plastic primer and enamel relative to the coil wire being exaggerated.

As an alternative to the seventh embodiment, the eighth embodiment of FIG. 11, generally designated 125, has heat shrinkable, axially elongated, annular heatable shrinkable Teflon bands (sheaths) positioned on an uncoated guidewire spring coil (axially spaced by the axial length of portion 101a) at the locations covered by coatings 105, 106 in FIG. 8, thence heated to shrink sufficiently to remain in place on the coil, then the combination of spring coil and the axially spaced heat shrinkable bands sprayed with non-heat shrinkable Teflon primer and thence with a non-heat shrinkable heat curable Teflon coatings such as previously described, and thereafter the curable coating is cured. During the curing, the heat shrinkable bands and the non-heat shrinkable coatings on the bands tears from the spring coil to leave a non-heat shrinkable Teflon band 126 on coil portion 127a that is directly adhered to said portion 127a to provide the desired indicia (mark) while coil portions 127b and 127c on axial opposite sides of portion 127a are uncoated.

In accordance with the method referred to in the preceding two paragraphs a heat shrinkable plastic band that has a sufficiently larger diameter than the coil to be easily axially positioned on the coil, for example positionable on a coil of a 0.045 inch diameter, and is heat shrinkable to a recovery size to form a close fit on a 0.020" coil so that the film breaks or tears when heat shrunk on a 0.45" diameter coil. The primer, if used, and the non-heat shrinkable plastic enamel is of a type that is heat curable, won't bleed into the plastic band when being cured and won't undesirably deteriorate while being heated to a high enough temperature that the heat shrinkable band will tear or break so that the heat shrinkable band and the coating of the film on the band will separate from the coil by the heating step for curing the coating, but only after the heat curable film has sufficiently cured to remain intact on the coil at the desired locations. Similarly the heat shrinkable band is of a type of plastic that will remain in place on the coil until after the curable plastic cures sufficiently to remain in place and thence will break, for example when heated to about 750° F. for the curing step, so that the heat shrinkable band and the non-heat shrinkable film surrounding the band breaks away from the coil. Of course the resulting guidewire has to be non-toxic and bio-compatible.

Even though in FIG. 8 only one annular portion of the resulting guidewire is shown being uncoated, it is to be understood that more than one annular portion can be uncoated to provide more than one indicia by using more than one heat shrinkable band fixed to the spring coil in axial spaced relationship and following the other steps set forth relative to the seventh embodiment. Similarly by positioning more than two axially spaced heat shrinkable bands on the spring coil and the other steps followed set forth relative to the eighth embodiment, the resulting guidewire will have more than one non-heat shrinkable band 126 in axially spaced relationship to each other on the coil and thereby provide more than one indicia on the guidewire member.

Even though this invention has been described with reference to guidewires having proximal beads, it is to be understood that guidewires without proximal beads can be provided with indicia such as described, for example on guidewires such as disclosed in U.S. Pat.

No. 4,799,496 that is assigned to the Assignee of this application. The indicia provided on such a guidewire would represent indicia representing progressively higher units in a direction from the distal end toward the proximal end.

What is claimed is:

1. A guidewire having an axially elongated guidewire member adapted for insertion into a vascular vessel or into a catheter that is inserted into a vascular vessel or the like, comprising an axially elongated guidewire member having a proximal end portion and a circumferential outer surface that extends the length thereof, and a plurality of axially spaced indicia on the circumferential surface to facilitate the determination of the axial length of the guidewire that is extended into at least one of the vessel and the catheter, the guidewire member having an axially elongated linear part having axially opposite first and second ends the plurality of indicia including a first series of indicia that represents one of progressively higher and lower units of measurement from the first end toward the second end and a second series of indicia that represents the other of progressively higher and lower units of measurement from the second end toward the first end.

2. A guidewire having an axially elongated guidewire member adapted for insertion into a vascular vessel or into a catheter that is inserted into a vascular vessel or the like, comprising an axially elongated guidewire member having a proximal end portion and a circumferential outer surface that extends the length thereof, and a plurality of axially spaced indicia on the circumferential surface to facilitate the determination of the axial length of the guidewire that is extended into at least one of the vessel and the catheter, the guidewire member comprising an axially elongated linear spring coil having a distal terminal end and a proximal terminal end, a distal tip joined to the distal terminal end and a proximal tip joined to the proximal terminal end the plurality of indicia including a first series of indicia on the spring coil axially more closely adjacent to the proximal tip than the distal tip and a second series of indicia located on the spring coil axially more closely adjacent to the distal tip than the proximal tip and a third indicium on the spring coil to indicate the axial center part of the coil, the first series of indicia including axially spaced marks representing progressively higher units of measurement in an axial direction from the proximal tip toward the third indicium and that the second series of indicia includes axially spaced marks representing progressively higher units of measurement in an axial direction from the distal tip toward the third indicium.

3. A guidewire having an axially elongated guidewire member adapted for insertion into a vascular vessel or into a catheter that is inserted into a vascular vessel or the like, comprising an axially elongated guidewire member having a proximal end portion and a circumferential outer surface that extends the length thereof, and a plurality of axially spaced indicia on the circumferential surface to facilitate the determination of the axial length of the guidewire that is extended into at least one of the vessel and the catheter, the guidewire member including a spring coil having a generally J-shaped part and a distal terminal end and an axially elongated linear coil part having a proximal terminal end and a distal terminal end integrally joined to the J-shaped part, a distal tip joined to the J-shaped distal terminal end and a proximal tip joined to the linear coil portion, the plurality of indicia being provided on the linear part, the plurality of indicia on the linear part including a series of indicia that represent progressively higher units of measurements from one of the linear coil part proximal terminal end and distal terminal end toward the other.

4. A method of treating a guidewire having an axially elongated guidewire member having axially elongated coil spring and axially opposite distal and proximal ends to facilitate ascertaining the distance that the guidewire extends into a vascular vessel or catheter or similar medical instruments, the steps of positioning at least one band of heat shrinkable plastic material such as polytetrofluoroethylene on the coil spring axially intermediate said ends, heating the heat shrinkable sufficiently so that the heat shrinkable band remains in a desired fixed axial position on the coil spring, applying a coating of nonheat shrinkable, heat curable plastic to cover the combination of the coil spring and the heat shrinkable band and thereafter heating the coated combination of coil and band to cure the curable film and to further shrink the band sufficiently to tear the band to break away from the coil spring after the heat curable coating has cured sufficiently to remain intact on the spring coil whereby the band and the non-heat shrinkable part of the coating thereon separate from the coil spring to provide indicia on the coil spring.

5. The method of claim 4 wherein the coil spring has an axial intermediate portion, a second portion extending distally of the intermediate portion and a third portion extending proximally of the intermediate portion, further characterized in that the band is positioned on the axial intermediate portion and that axial intermediate portion is left uncoated after the heat curing step.

6. The method of claim 4 wherein the coil spring has an axial intermediate portion, a second portion extending distally of the intermediate portion and a third portion extending proximally of the intermediate portion, further characterized in that the step of placing at least one band comprises positioning a first heat shrinkable band on the coil spring second portion and a second band on the third portion and that the step of applying the coating includes applying the coating to the intermediate portion axially between the first and second bands whereby after the curing step the coating remains on the intermediate portion while the distal and proximal portions are uncoated.

7. The method of claim 4 wherein the band is made of a water base polytetrofluoroethylene material, that the coating step includes applying a water base polytetrofluoroethylene primer and thereafter a water base polytetrofluoroethylene enamel and that the curing step includes heating to a temperature of about 750° F.

* * * * *